United States Patent
Huang

(10) Patent No.: US 12,226,651 B2
(45) Date of Patent: *Feb. 18, 2025

(54) METHOD AND SYSTEM FOR PHOTOBIOMODULATED EXOSOME AND STEM CELL THERAPY

(71) Applicant: Li-Da Huang, Austin, TX (US)

(72) Inventor: Li-Da Huang, Austin, TX (US)

( * ) Notice: Subject to any disclaimer, the term of this patent is extended or adjusted under 35 U.S.C. 154(b) by 1060 days.

This patent is subject to a terminal disclaimer.

(21) Appl. No.: 16/992,076

(22) Filed: Aug. 12, 2020

(65) Prior Publication Data

US 2021/0023385 A1    Jan. 28, 2021

Related U.S. Application Data

(63) Continuation-in-part of application No. 15/861,504, filed on Jan. 3, 2018, now Pat. No. 10,821,298.

(60) Provisional application No. 62/885,766, filed on Aug. 12, 2019.

(51) Int. Cl.
| | |
|---|---|
| *A61N 5/06* | (2006.01) |
| *A61K 35/28* | (2015.01) |
| *A61K 41/00* | (2020.01) |
| *A61N 5/067* | (2006.01) |

(52) U.S. Cl.
CPC .............. *A61N 5/062* (2013.01); *A61K 35/28* (2013.01); *A61K 41/00* (2013.01); *A61N 2005/0628* (2013.01); *A61N 2005/066* (2013.01); *A61N 2005/0663* (2013.01); *A61N 5/067* (2021.08)

(58) Field of Classification Search
CPC ........ A61N 5/06; A61N 5/062; A61N 5/0622; A61N 5/0624; A61N 2005/0626; A61N 2005/0627; A61N 2005/0628; A61N 2005/0642; A61N 2005/065; A61N 2005/0651; A61N 2005/0652; A61N 2005/0658; A61N 2005/0659; A61N 2005/0662; A61N 5/067; A61K 35/12; A61K 35/32; A61K 35/56
USPC ...................................................... 607/88–91
See application file for complete search history.

(56) References Cited

U.S. PATENT DOCUMENTS

| | | | | |
|---|---|---|---|---|
| 10,434,328 B2* | 10/2019 | Gilson | ............... | A61N 5/0622 |
| 10,821,298 B2* | 11/2020 | Huang | ............... | A61N 5/0622 |
| 11,771,917 B2* | 10/2023 | Huang | ............... | A61N 5/062 |
| | | | | 607/88 |
| 2014/0364721 A1* | 12/2014 | Lee | ........... | A61N 5/062 |
| | | | | 600/411 |
| 2016/0067087 A1* | 3/2016 | Tedford | ............... | A61N 5/0624 |
| | | | | 606/4 |

* cited by examiner

*Primary Examiner* — Ahmed M Farah
(74) *Attorney, Agent, or Firm* — Ying-Ting Chen; Law Office of Michael Chen

(57) ABSTRACT

In one aspect, a system for in vivo stimulation of targeted tissues of a subject integrated in Exosome and/or stem cell therapies may include at least one light source, a controller to control operation of the light source, a signal detecting unit and a processor configured to receive signals from the signal detecting unit, analyze the signals and generate a feedback signal to the controller to control the light source until optimal results are obtained. In one embodiment, the light source is a laser instrument and the wavelength can range from 400 to 1100 nm. In another embodiment, the irradiance of the laser instrument can range from 10 to 3000 mW/cm$^2$.

9 Claims, 8 Drawing Sheets

METHOD AND SYSTEM FOR PHOTOBIOMODULATED EXOSOME AND STEM CELL THERAPY

CROSS-REFERENCE TO RELATED APPLICATIONS

This application claims priority under 35 U.S.C. § 119 (e) to U.S. Provisional Patent Application Ser. No. 62/885,766, filed on Aug. 12, 2019; this application is also a continuation-in-part (CIP) application of Ser. No. 15/861,504 filed on Jan. 3, 2018, the entire contents of which are hereby incorporated by reference.

FIELD OF THE INVENTION

The present invention relates to a method and apparatus for tissue function enhancement, and more particularly to a photobiomodulation conducted with predetermined dosage, timing and location of the stimulation of the tissue in exosome and stem cell therapy.

BACKGROUND OF THE INVENTION

Photobiomodulation involves the absorption of photons and the subsequent modulation of metabolic processes in cells, including neurons. For red to near-infrared light, the major intracellular molecule absorbing photons is cytochrome c oxidase (CCO), a mitochondrial respiratory enzyme that can be upregulated in vitro and in vivo. Upregulation of CCO serves to convert high-energy photons into a source for ATP-based metabolic energy production in the brain as shown in FIG. 1. Photobiomodulation of neural functions has been successful at 633-1070-nm wavelengths.

Exosomes are so-called extracellular vesicles, or small bubbles, released from cells, especially from stem cells. They act as shuttles for certain genetic information and proteins to other cells. Also, they allow for cell-to-cell communication, transporting molecules that are important regulators of intracellular information between close and distant cells. They carry information from place to place with different functions and purposes telling cells how and when to react.

Exosome therapy is one of the hottest areas of regenerative medicine treatment. While stem cells are usually responsible for rejuvenation of older cells, they may not be able to supply all the information needed. So, supporting Exosome function could have a greater positive effect, by providing a new piece of information to enhance the healing process.

Exosome therapy is a minimally invasive procedure commonly used in orthopedic injuries, for anti-aging and other degenerative diseases. Exosome treatment contains growth factors, messenger RNA, micro RNA, cytokines and other biologically active molecules in conjunction with stem cell therapy to speed up healing benefit.

However, current Exosome and stem cell therapies do not incorporate a feedback control mechanism to generate an optimal dosage, timing and location of targeted tissues. Therefore, there remains a need for a new and improved photobiomodulated method and system for to stimulate target tissues before, during and after Exosome and stem cell therapies to enhance the therapeutic effects.

SUMMARY OF THE INVENTION

It is an object of the present invention to provide a method and system to stimulate targeted tissues before, during and after Exosome and stem cell therapies to enhance the therapeutic effects.

It is another object of the present invention to provide a method and apparatus to enhance therapeutic effects of Exosome and stem cell therapies, wherein a photobiomodulation is conducted with predetermined dosage, timing and location to stimulate targeted tissues.

It is a further object of the present invention to provide a method and apparatus to enhance therapeutic effects of Exosome and stem cell therapies wherein a feedback loop control is implemented to achieve optimal therapeutic results.

In one aspect, a system for in vivo stimulation of targeted tissues of a subject integrated in Exosome and/or stem cell therapies may include at least one light source, a controller to control operation of the light source, a signal detecting unit; and a processor configured to receive signals from the signal detecting unit, analyze the signals and generate a feedback signal to the controller to control the light source, wherein the detected signal is processed through Fourier Transform (FT) with at least one predetermined time window, which is divided by the value of the detected signal transformed by FT and integrated for a predetermined bandwidth to generate a normalized FT signals to compare with one existing signals saved in a memory unit in the processor to determine and generate the feedback signal. In one embodiment, the processor can also be configured to extract feature points to feed into at least one machine learning algorithms to learn and identify tissue status. It is noted that the feature points include, but no limited to peaks and valleys of the normalized FT signals, including the frequencies, amplitudes, bandwidth of the integration for normalization, the integration values, the time window to get the FT and the duration of the normalized FT spectrum.

In one embodiment, the light source is a laser instrument and the wavelength thereof can range from 400-1100 nm. In another embodiment, the irradiance of the laser instrument can range from 10-3000 $mW/cm^2$; and the laser can be directed at the targeted tissues. The laser aperture can be adjusted to a desired spot size from the diameter from 1 to 45 mm.

In a further embodiment, the detecting unit is configured to detect the tissue activity through ultrasonic signals, functional magnetic resonance imaging (fMRI) images, broadband near-infrared spectroscopy (bbNIRS) signals, and blood-oxygen-level-dependent (BOLD) data, etc., and the detected data or signals are transmitted to the processor to analyze to determine whether the dosage, timing and location of the tissue stimulation has to be adjusted, and the feedback loop control can be conducted for one or more times until the optimal results are obtained.

In another aspect, a method for in vivo stimulation of targeted tissues of a subject integrated in Exosome and/or stem cell therapies may include steps of providing at least one light source, placing the light source near the targeted tissues of the subject to stimulate the targeted tissues; detecting signals before and after the tissue stimulation; and analyzing detected signals and generating a feedback loop control to adjust dosage, timing and location of the light source based on the analyzed results, wherein the step of generating a feedback control signal includes steps of conducting Fourier Transform on detected signals in at least one predetermined time window for a predetermined bandwidth, integrating the Fourier transformed signals for the predetermined bandwidth, generating a normalized signal by dividing the integrated Fourier transformed signals with the Fourier transformed signals, and comparing the normalized signal with at least one existing signal to generate the feedback control signal.

BRIEF DESCRIPTION OF THE DRAWINGS

FIG. 1 is cited from "Up-regulation of cerebral cytochrome-c-oxidase and hemodynamics by transcranial infrared laser stimulation: A broadband near-infrared spectroscopy study" published at Journal of Cerebral Blood Flow & Metabolism in December 2017.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

Figure 1:
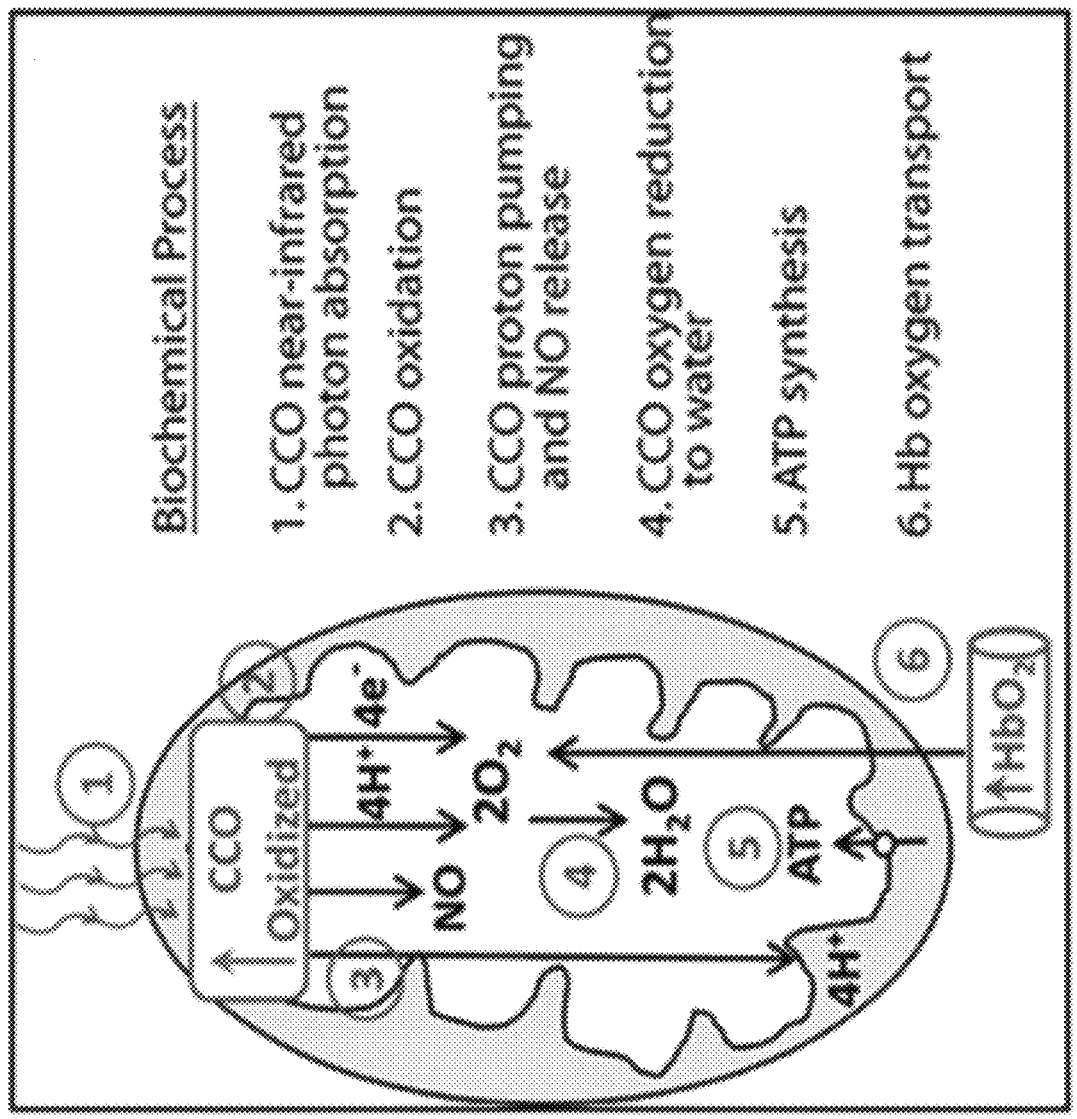
FIG. 1 is a schematic view of a mechanism of a mitochondrial respiratory enzyme cytochrome c oxidase (CCO) to convert high-energy photons into a source for ATP-based metabolic energy production in the brain.
Figure 2:
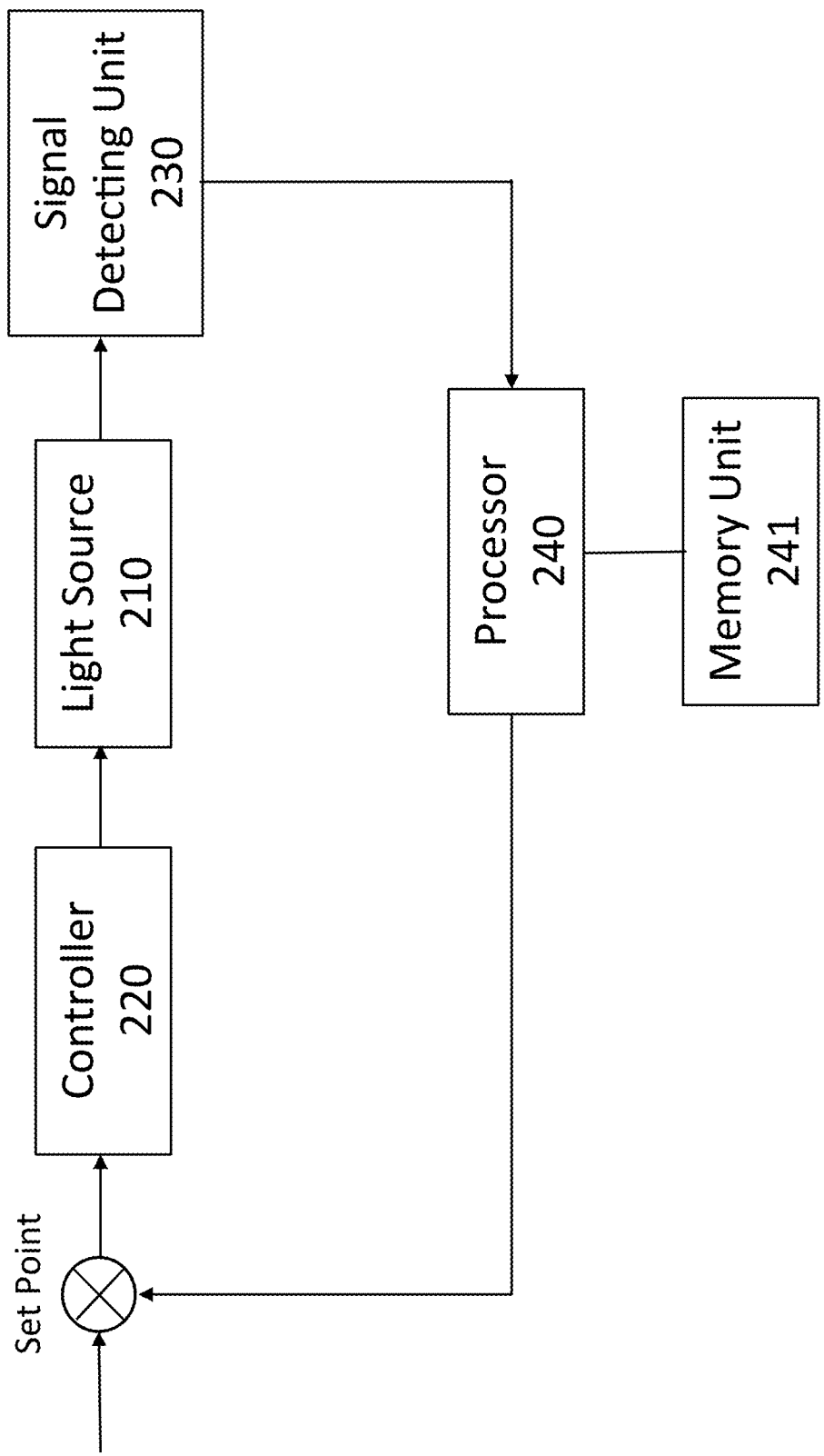
FIG. 2 is a schematic view of the feedback loop control of the system for in vivo stimulation of targeted tissues of a subject integrated in an Exosome and stem cell therapies in the present invention.
Figure 3:
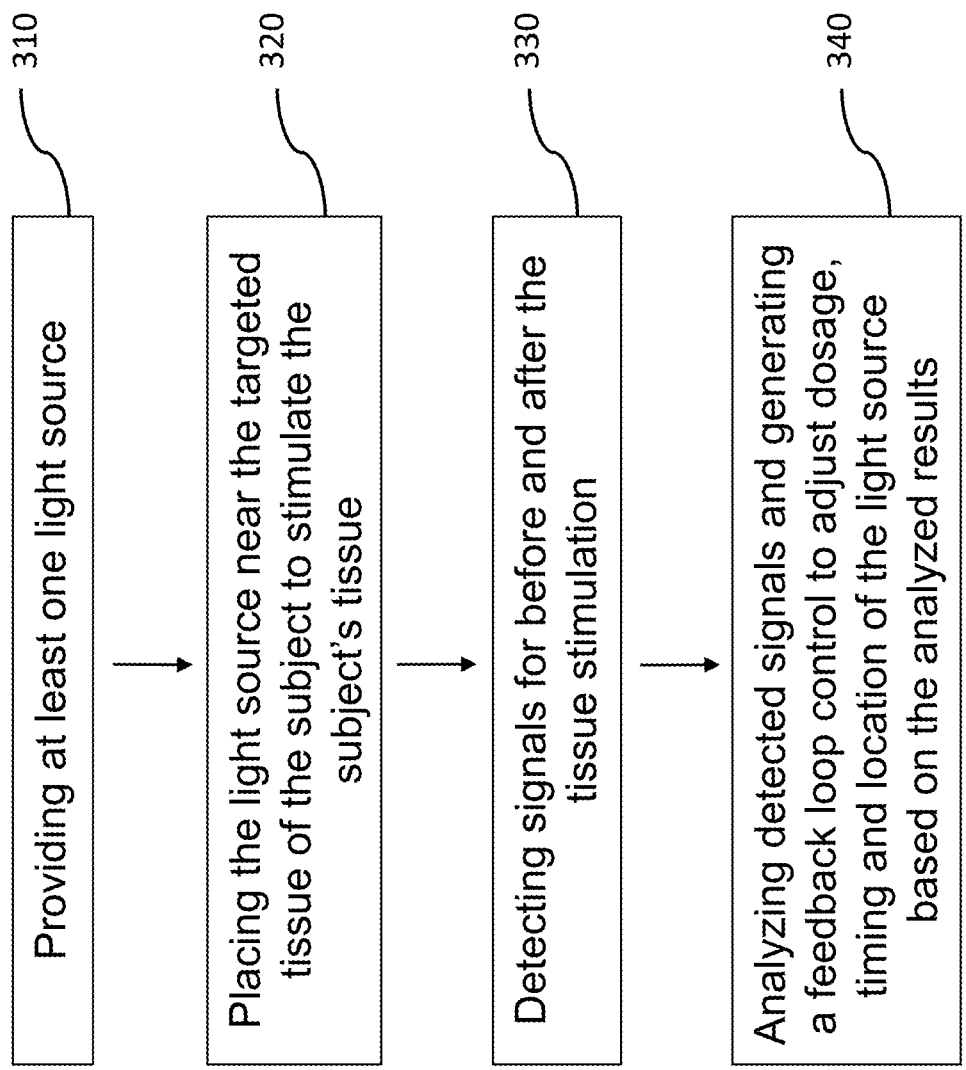
FIG. 3 illustrates a block diagram of a method for in vivo stimulation of targeted tissues of a subject in the present invention.

In one aspect, as shown in FIG. 2, a system 200 for in vivo stimulation of targeted tissues of a subject integrated in Exosome and/or stem cell therapies may include at least one light source 210, a controller to control operation of the light source 220, a signal detecting unit 230 and a processor 240 configured to receive signals from the signal detecting unit 230, analyze the signals and generate a feedback signal to the controller 220 to control the light source 210, wherein the detected signal is processed through Fourier Transform (FT) with at least one predetermined time window, which is divided by the value of the detected signal transformed by FT and integrated for a predetermined bandwidth to generate a normalized FT signals to compare with one existing signals saved in a memory unit 241 in the processor 240 to determine and generate the feedback signal. In one embodiment, the processor 240 can also be configured to extract feature points to feed into at least one machine learning algorithms to learn and identify targeted tissue status. It is noted that the feature points include, but no limited to peaks and valleys of the normalized FT signals, including the frequencies, amplitudes, bandwidth of the integration for normalization, the integration values, the time window to get the FT and the duration of the normalized FT spectrum.

As stated above, the present invention is configured to conduct a photobiomodulation with predetermined dosage, timing and location of the stimulation of the targeted tissues. More specifically, the present invention is configured to use infrared photons to oxidize cytochrome c oxidase (CCO) in the targeted tissues to activate the targeted tissues and eventually enhance therapeutic effects of Exosome and stem cell therapies. In one embodiment, the light source 210 is a laser instrument and the wavelength thereof can range from 400-1100 nm. In one embodiment, the laser has a homogeneous beam power distribution achieved by an optical lens system mounted on the handpiece as measured at 1064 nm by an optical power meter (Model 1916-C) and photodiode detectors (Model 918D/918L) manufactured by Newport (Newport Corp., Irvine, CA, USA) that systematically measured each spot of the beam area with independent and overlapping 0.44 to 1-$cm^2$ detectors.

Regarding the laser dose, in one embodiment, the laser wave was continuous (CW), and the power output used was 3.4 W for all treated groups. In another embodiment, the laser wave can be pulsed. The irradiance (power density) used for all treated groups was 250 mW/$cm^2$ (3400 mW/13.6 $cm^2$=250 mW/$cm^2$) and the laser dose can be adjusted by the controller 220 from 10 to 3000 mW/$cm^2$. For cognitive and fMRI studies, the laser exposure time was 240 second per site for two forehead sites, and thus, the fluence dose (energy density) used was 60 J/cm$^2$ (0.25 W/cm$^2$×240 second=60 J/cm$^2$) per site. Therefore, for the cognitive and fMRI studies, the forehead cumulative fluence dose per session was 220 J/cm$^2$ (60 J/cm$^2$×2 forehead sites=220 J/cm$^2$). It is noted that these are the same parameters that previously showed psychologically beneficial effects.

The laser stimulation was alternated every minute between these sites to prevent heating of the skin and to fractionate the dose for a total of 4 minutes per site (3.4 W×240 s=816 J/site). In one embodiment, the total treatment duration can be lasted for 8 minutes for each session and repeated weekly for 5 weeks.

In another embodiment, the signal detecting unit 230 is configured to obtain ultrasound scan images. For example, the ultrasound scan images can be obtained using a GE LOGIQ e Ultrasound System, and subsequently the ultrasound images can be analyzed by the processor 240. For example, ultrasound images can be analyzed by a computerized image analysis software (Vascular Research Tool Carotid Analyzer, Medical Imaging Applications, Coralville, IA). Carotid IMT is defined as the distance between the leading edge of the lumen-intima interface and the leading edge of the media-adventitia interface of the far wall.

In still another embodiment, the signal detecting unit 230 can be configured to obtain the subject's fMRI Imaging data. For instance, anatomical scans were collected in the sagittal plane using a high-resolution ultrafast gradient echo 3D (MPRAGE) sequence (256×256 matrix, flip angle=7°, field of view (FOV)=24×24 cm$^2$, 1-mm slice thickness, 0 gap). All EPI images were processed by the processor 240. For example, the EPI images can be analyzed with Analysis of Functional Neuro Images (AFNI) software. Each time series was spatially registered to the sixth volume of the session.

In a further embodiment, the signal detecting unit 230 can be used to detect Blood-Oxygen-Level-Dependent (BOLD) data. It is noted that the blood oxygen level can also be detected by functional near-infrared spectroscopy (fNIRS). In still a further embodiment, the signal detecting unit 230 can be used to detect the concentration of oxidize cytochrome c oxidase (CCO). In some embodiments, the signal detecting unit 230 can be used to detect broadband near-infrared spectroscopy (bbNIRS) signals.

It is important to note that the present invention provides a feedback loop control to control the dosage, timing and location of the stimulation of the tissue, as shown in FIG. 2. For example, an initial dosage of the light source 210, e.g. laser, can be provided to start the process of tissue stimulation. The detecting unit 230 is configured to detect the tissue activity through ultrasonic signals, functional magnetic resonance imaging (fMRI) images, broadband near-infrared spectroscopy (bbNIRS) signals, and blood-oxygen-level-dependent (BOLD) data, etc., and the detected data or signals are transmitted to the processor 240 to analyze to determine whether the dosage, timing and location of the tissue stimulation has to be adjusted, and the feedback loop control can be conducted for one or more times until the optimal results are obtained.

It is also noted that the physiological response of the cells or the tissues of the target area are collected and feedback to the light source and the control module in order to adjust the light intensity, wavelength, target location and shape. Also, the photobiomodulation treatment could be applied prior to the exosomes therapy to prime the tissue by activating the mitochondria activities. It could also be applied during the exosomes therapy to guide the cell interaction with the exosomes. Furthermore, it could be applied after the therapy to consolidate the results. The photobiomodulation could be also applied to inhibit the mitochondria activities in order to constrain the exosomes therapy in a bounded region.

In another aspect, a method for in vivo stimulation of targeted tissues of a subject integrated in Exosome and/or stem cell therapies may include steps of providing at least one light source 310, placing the light source near the targeted tissues of the subject to stimulate the targeted tissues 320; detecting signals for before and after the tissue stimulation 330; and analyzing detected signals and generating a feedback control signal to adjust dosage, timing and location of the light source based on the analyzed results 340, wherein the step of analyzing detected signals and generating a feedback control signal 340 includes steps of conducting Fourier Transform on detected signals in at least one predetermined time window for a predetermined bandwidth 341, integrating the Fourier transformed signals for the predetermined bandwidth 342, generating a normalized signal by dividing the integrated Fourier transformed signals with the Fourier transformed signals 343, and comparing the normalized signal with at least one existing signal to generate the feedback control signal 344.

In one embodiment, the step of analyzing detected signals and generating a feedback control signal 340 may further include a step of extracting feature points to feed into at least one machine learning algorithms to learn and identify tissue status 350. It is noted that the feature points include, but no limited to peaks and valleys of the normalized FT signals, including the frequencies, amplitudes, bandwidth of the integration for normalization, the integration values, the time window to get the FT and the duration of the normalized FT spectrum.

In another embodiment, the light source in step 310 is a laser instrument wherein the wavelength thereof can range from 400 to 1100 nm and the irradiance of the laser instrument is 10 to 3000 mW/cm$^2$. In a further embodiment, in step 320, the laser can be directed at the targeted tissues, and the laser aperture can be adjusted to a desired spot size from the diameter from 1 to 45 mm.

Figure 4:
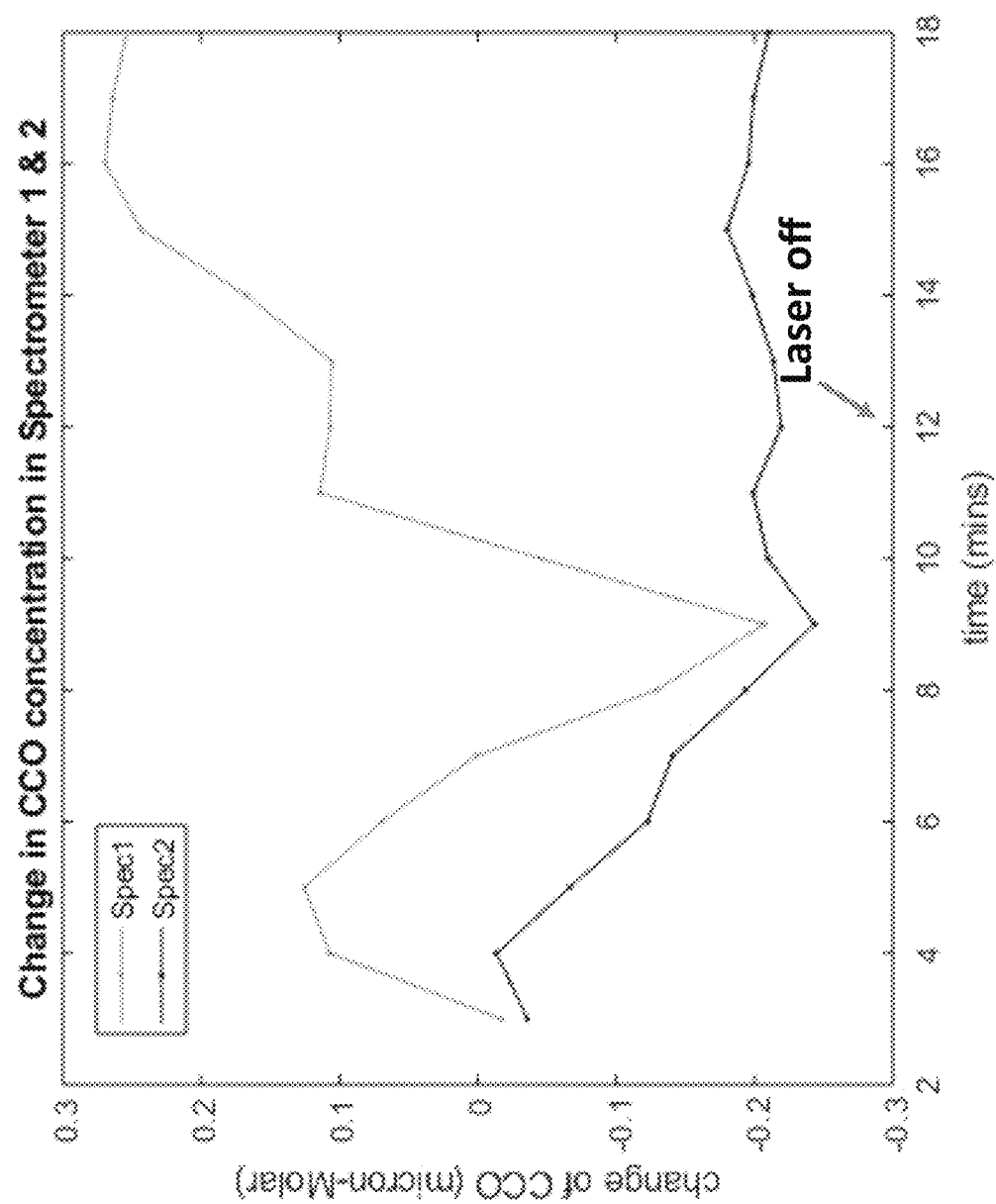
FIG. 4 illustrates the broadband near-infrared spectroscopy (bbNIRS) signals regarding the change of CCO concentration in a superficial portion and a deep portion of a targeted tissue under photobiomodulation.

In still a further embodiment, the step of detecting signals for before and after the tissue stimulation 330 may include the step of detecting the tissue activity through ultrasonic signals, functional magnetic resonance imaging (fMRI) images, broadband near-infrared spectroscopy (bbNIRS) signals, and blood-oxygen-level-dependent (BOLD) data, etc., and step 340 is configured to receive and analyze the detected data or signals to determine whether the dosage, timing and location of the tissue stimulation has to be adjusted, and the feedback loop control can be conducted for one or more times until the optimal results are obtained. The "Results" section below shows the change of tissue behavior after conducting photobiomodulation that can be used to optimize Exosome and stem cell therapies Results FIG. 4 illustrates the results of broadband near-infrared spectroscopy (bbNIRS) signals regarding the change of CCO concentration in a targeted tissue under photobiomodulation in a predetermined time period. It is noted that Spectrometer 1 (or Spec1) indicates the bbNIRS signals in a superficial portion of the targeted tissue, while Spectrometer 2 (or Spec2) indicates the bbNIRS signals in a deep portion of the targeted tissue. It is also noted that the change in CCO here can indicate the degree of tissue activation under photobiomodulation. Namely, the more CCO increases in the tissue, the higher the degree of tissue activation.

In FIG. 4, the results indicate that more CCO increases in the superficial targeted tissue than in the deep portion thereof under photobiomodulation, even after the laser is off at about 12 minutes. The results in FIG. 4 can provide a message that since the deep portion of the targeted tissue is more difficult to activate, it may need more dosage when further conducting Exosome and/or stem cell therapies.

Figure 5:
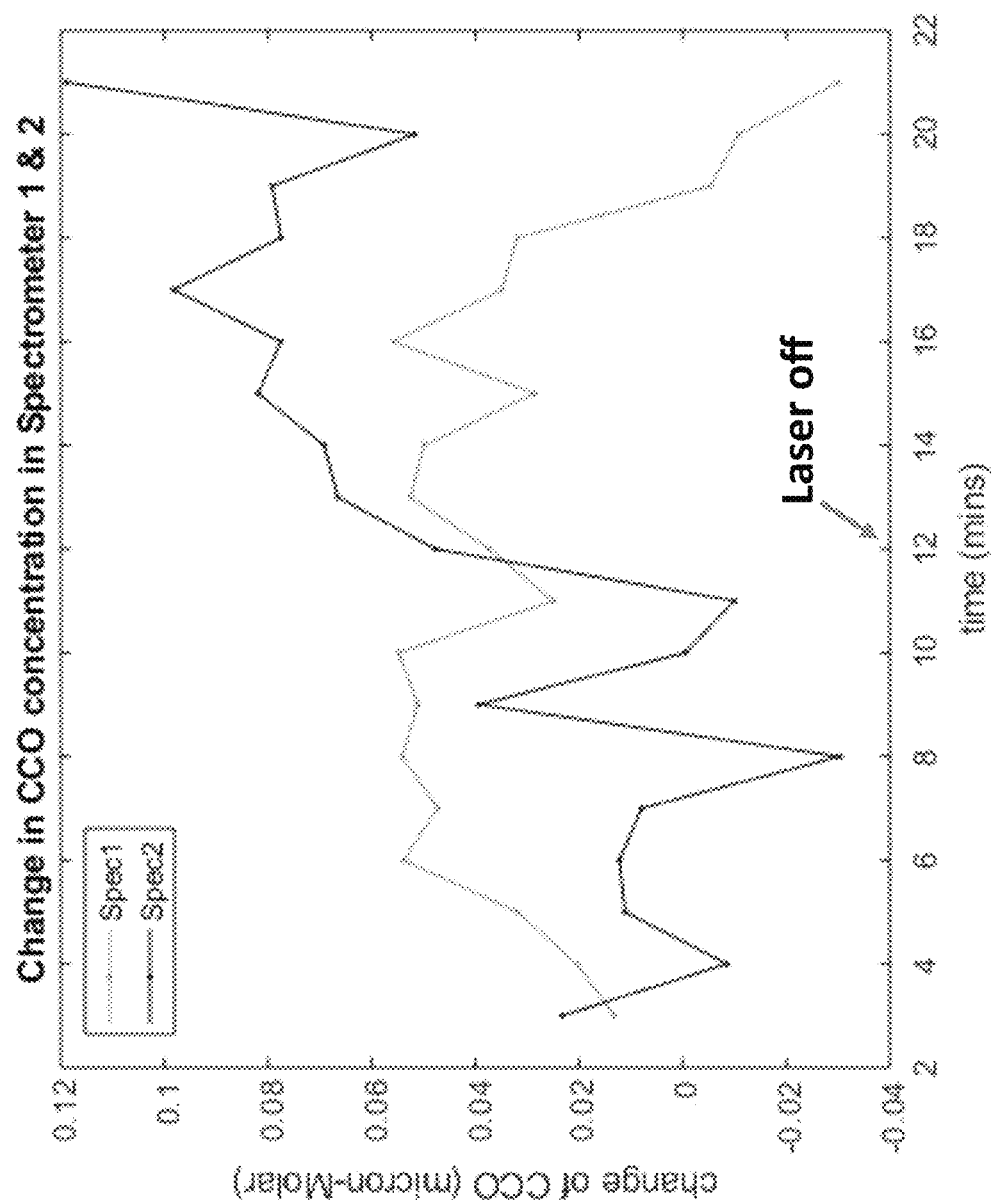
FIG. 5 illustrates the bbNIRS signals regarding the change of CCO concentration in a superficial portion and a deep portion of a different targeted tissue under photobiomodulation.

FIG. 5 shows the results of another targeted tissue in superficial/deep portions under photobiomodulation. As shown in FIG. 5, the increase in CCO in the deep portion targeted tissue is slower than the superficial portion under photobiomodulation, meaning the deep portion tissue does not respond well under photobiomodulation. However, after the laser is off, the deep portion tissue begins to respond and the degree of activation is much higher than the superficial portion tissue, which may indicate that the deep portion tissue is old and slowly activated. So, before further conducting Exosome and/or stem cell therapies, the deep portion tissue may need some pre-conditioning to be more activated to enhance the therapeutic effect.

Figure 6:
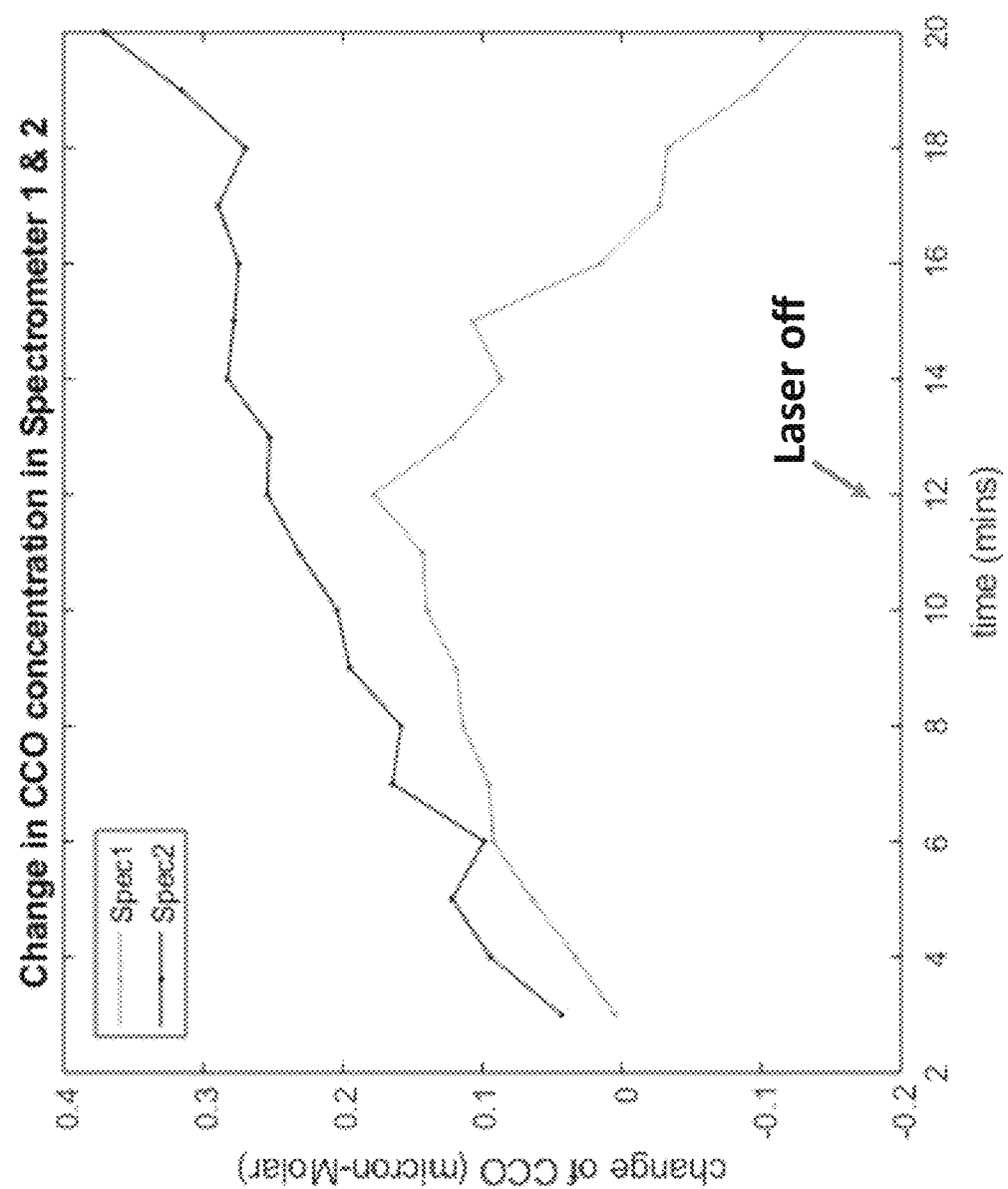
FIG. 6 illustrates the bbNIRS signals regarding the change of CCO concentration in a superficial portion and a deep portion of a different targeted tissue under photobiomodulation.
Figure 7:
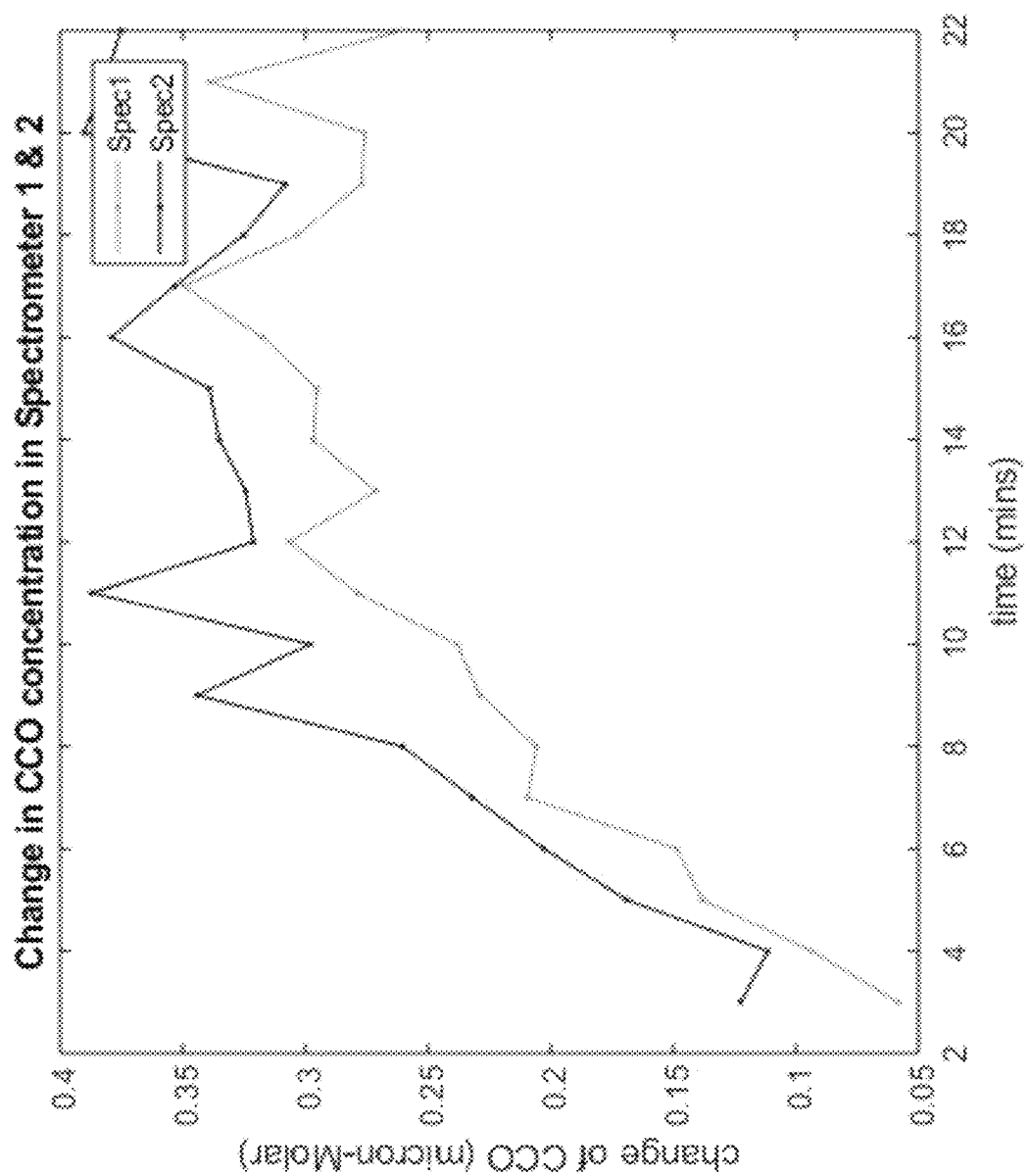
FIG. 7 illustrates the bbNIRS signals regarding the change of CCO concentration in a superficial portion and a deep portion of a different targeted tissue under photobiomodulation.

FIG. 6 shows the results of a different targeted tissue in superficial/deep portions under photobiomodulation. Unlike FIG. 4, the deep portion of this targeted tissue can be more easily activated than the superficial portion thereof, so the dosage of Exosome and/or stem cell therapies can be adjusted according to the degree of activation on the deep/superficial portion of the tissue. FIG. 7 shows the results of a probably younger tissue in superficial/deep portions under photobiomodulation because the tissues in both superficial and deep portions are very responsive under photobiomodulation.

Figure 8:
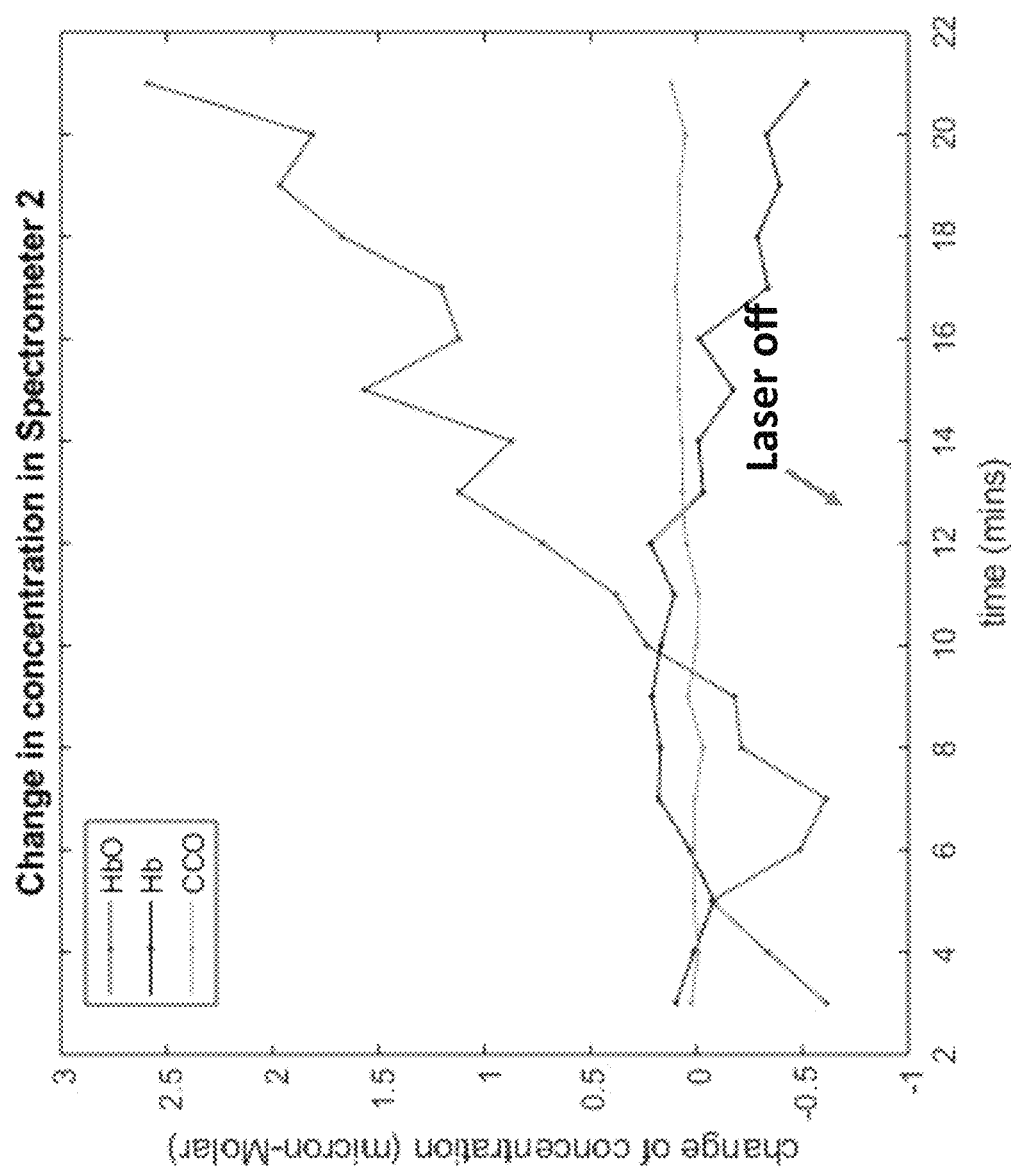
FIG. 8 illustrates the change of concentration of HbO (Hemoglobin with oxygen), Hb (Hemoglobin without oxygen) and CCO of a deep targeted tissue.

FIG. 8 shows the change of concentration of HbO (Hemoglobin with oxygen), Hb (Hemoglobin without oxygen) and CCO of a deep targeted tissue. It is noted that the concentration increase of HbO can also indicate higher degree of tissue activation. As shown in FIG. 8, the concentration of HbO concentration does not increase until the nineth minutes, and significantly increases afterwards, which means the tissue begins to be activated.

Having described the invention by the description and illustrations above, it should be understood that these are exemplary of the invention and are not to be considered as limiting. Accordingly, the invention is not to be considered as limited by the foregoing description, but includes any equivalent.

What is claimed is:

1. A system for in vivo stimulation of a targeted tissue of a subject integrated in Exosome and/or stem cell therapies comprising at least one light source, a controller to control operation of the light source, a signal detecting unit and a processor configured to receive a signal from the signal detecting unit, analyze the signal and generate a feedback signal to the controller to control the light source until optimal results are obtained,
   wherein the detected signal is processed through Fourier Transform (FT) with at least one predetermined time window, which is divided by the value of the detected signal transformed by FT and integrated for a predetermined bandwidth to generate a normalized FT signals to compare with one existing signals saved in a memory unit in the processor to determine and generate the feedback signal,
   wherein the processor is configured to extract feature points to feed into at least one machine learning algorithms to learn and identify tissue status, and the feature points include, but no limited to peaks and valleys of the normalized FT signals, including the frequencies, amplitudes, bandwidth of the integration for normalization, the integration values, the time window to get the FT and the duration of the normalized FT spectrum.

2. The system for in vivo stimulation of a targeted tissue of a subject integrated in Exosome and/or stem cell therapies of claim 1, wherein the light source is a laser instrument.

3. The system for in vivo stimulation of a targeted tissue of a subject integrated in Exosome and/or stem cell therapies of claim 2, wherein a wavelength of the laser instrument is 400 to 1100 nm.

4. The system for in vivo stimulation of a targeted tissue of a subject integrated in Exosome and/or stem cell therapies of claim 2, wherein an irradiance of the laser instrument is 10 to 3000 $mW/cm^2$.

5. The system for in vivo stimulation of a targeted tissue of a subject integrated in Exosome and/or stem cell therapies of claim 1, wherein the detecting unit is configured to detect the subject's ultrasonic signals, functional magnetic resonance imaging (fMRI) images, broadband near-infrared spectroscopy (bbNIRS) signals, and blood-oxygen-level-dependent (BOLD) data.

6. The system for in vivo stimulation of a targeted tissue of a subject integrated in Exosome and/or stem cell therapies of claim 1, wherein the light source can be any controlled light source with controllable wavelength, power, frequency etc.

7. A method for in vivo stimulation of a targeted tissue of a subject integrated in Exosome and/or stem cell therapies comprising steps of providing at least one light source, placing the light source near the targeted tissues of the subject to stimulate the targeted tissues; detecting signals before and after the tissue stimulation; analyzing detected signals; and generating a feedback control signal to adjust dosage, timing and location of the light source based on the analyzed results,
   wherein the step of generating a feedback control signal includes steps of conducting Fourier Transform on detected signals in at least one predetermined time window for a predetermined bandwidth, integrating the Fourier transformed (FT) signals for the predetermined bandwidth, generating a normalized signal by dividing the integrated Fourier transformed signals with the Fourier transformed signals, and comparing the normalized signal with at least one existing signal to generate the feedback control signal,
   wherein the step generating a feedback control signal further comprises a step of extracting feature points to feed into at least one machine learning algorithms to learn and identify tissue status, and the feature points include, but no limited to peaks and valleys of the normalized FT signals, including the frequencies, amplitudes, bandwidth of the integration for normalization, the integration values, the time window to get the FT and the duration of the normalized FT spectrum.

8. The method for in vivo stimulation of a targeted tissue of a subject integrated in Exosome and/or stem cell therapies of claim 7, wherein the light source is a laser instrument; the wavelength thereof is 400 to 1100 nm and the irradiance thereof is 10 to 3000 $mW/cm^2$.

9. The method for in vivo stimulation of a targeted tissue of a subject integrated in Exosome and/or stem cell therapies of claim 7, wherein the step of detecting signals before and after the tissue stimulation includes the step of detecting the subject's ultrasonic signals, functional magnetic resonance imaging (fMRI) images, broadband near-infrared spectroscopy (bbNIRS) signals, and blood-oxygen-level-dependent (BOLD) data.

* * * * *